United States Patent
Jang et al.

(10) Patent No.: US 12,168,073 B2
(45) Date of Patent: Dec. 17, 2024

(54) PERCUTANEOUS ABSORPTION PREPARATION COMPRISING STABILIZED DONEPEZIL

(71) Applicants: DONG-A ST CO., LTD., Seoul (KR); KM TRANSDERM LTD., Osaka (JP)

(72) Inventors: Sun-Woo Jang, Seoul (KR); Chang-Yell Shin, Seoul (KR); Hae-Sun Kim, Hwaseong-Si (KR); Kwang-Ho Cha, Seoul (KR); Hyun-Jung Kim, Yongin-Si (KR); Masaoki Goto, Osaka (JP)

(73) Assignees: DONG-A ST CO., LTD., Seoul (KR); KM TRANSDERM LTD., Osaka (JP)

( * ) Notice: Subject to any disclaimer, the term of this patent is extended or adjusted under 35 U.S.C. 154(b) by 799 days.

(21) Appl. No.: 17/416,930

(22) PCT Filed: Sep. 5, 2019

(86) PCT No.: PCT/KR2019/011483
§ 371 (c)(1),
(2) Date: Jun. 21, 2021

(87) PCT Pub. No.: WO2020/130287
PCT Pub. Date: Jun. 25, 2020

(65) Prior Publication Data
US 2022/0047524 A1    Feb. 17, 2022

(30) Foreign Application Priority Data
Dec. 21, 2018   (KR) .................. 10-2018-0167289

(51) Int. Cl.
*A61K 9/70* (2006.01)
*A61K 31/445* (2006.01)
*A61K 47/20* (2006.01)

(52) U.S. Cl.
CPC .......... *A61K 9/7053* (2013.01); *A61K 31/445* (2013.01); *A61K 47/20* (2013.01)

(58) Field of Classification Search
None
See application file for complete search history.

(56) References Cited

U.S. PATENT DOCUMENTS

| | | | |
|---|---|---|---|
| 6,372,760 B1 | 4/2002 | Kato et al. | |
| 2008/0131490 A1* | 6/2008 | Hanatani | A61P 25/28 514/319 |
| 2008/0138388 A1 | 6/2008 | Aida et al. | |
| 2009/0291127 A1 | 11/2009 | Wen et al. | |
| 2012/0207816 A1 | 8/2012 | Kawakami et al. | |
| 2018/0008612 A1 | 1/2018 | Lee et al. | |
| 2021/0059956 A1 | 3/2021 | Jang et al. | |
| 2021/0251973 A1 | 8/2021 | Hakonarson et al. | |

FOREIGN PATENT DOCUMENTS

| | | |
|---|---|---|
| EP | 1 437 130 A1 | 7/2004 |
| EP | 2 098 233 A1 | 9/2009 |
| EP | 3 235 494 A1 | 10/2017 |
| KR | 10-0866720 B | 11/2008 |
| KR | 10-2009-0086565 A | 8/2009 |
| KR | 10-2009-0101667 A | 9/2009 |
| KR | 10-2012-0093293 A | 8/2012 |
| KR | 10-2013-0098902 A | 9/2013 |
| KR | 10-1408454 B | 6/2014 |
| KR | 10-1408500 B | 6/2014 |
| KR | 10-2016-0074433 A | 6/2016 |
| KR | 10-2016-0120778 A | 10/2016 |
| WO | 2015/111862 A1 | 7/2015 |
| WO | 2018/022817 A1 | 2/2018 |

OTHER PUBLICATIONS 3-mercaptopropane-1,2-diol, retrieved from the Internet on May 19, 2024 from https://-en.wikipedia.org/wiki/3-Mercaptopropane-1,2-diol. (Year: 2024).*
International Searching Authority, Written Opinion for PCT/KR2019/011483 dated Jan. 10, 2020.
International Searching Authority, International Search Report for PCT/KR2019/011483 dated Jan. 10, 2020.

* cited by examiner

*Primary Examiner* — David J Blanchard
*Assistant Examiner* — Daniel F Coughlin
(74) *Attorney, Agent, or Firm* — Sughrue Mion, PLLC

(57) ABSTRACT

A percutaneous absorption preparation including donepezil for the treatment of dementia is disclosed. The percutaneous absorption preparation for the treatment of dementia includes a support layer, a drug-containing layer, and a release layer, wherein the drug-containing layer contains donepezil or a pharmaceutically acceptable salt thereof as an active ingredient; monothioglycerol, thiocyanate metal salt (preferably potassium salt) or dimethylthiourea as a stabilizer; and a pressure-sensitive adhesive. Also disclosed is a percutaneous absorption preparation for the treatment of dementia with reduced the formation of donepezil impurities.

5 Claims, No Drawings

PERCUTANEOUS ABSORPTION PREPARATION COMPRISING STABILIZED DONEPEZIL

CROSS-REFERENCE TO RELATED APPLICATIONS

This application is a National Stage of International Application No. PCT/KR2019/011483 filed Sep. 5, 2019, which claims priority under U.S.C. § 119 (a) to Korean Patent Application No. 10-2018-0167289 filed on Dec. 21, 2018.

TECHNICAL FIELD

The present invention relates to a stabilized percutaneous absorption preparation comprising donepezil that has been stabilized to reduce the formation of impurities.

BACKGROUND ART

The "Guideline on quality of percutaneous patches" issued by the European Medicines Agency recommends that the standard of impurities in percutaneous preparations be controlled according to the ICH Q3B guidelines, published by the International Council for Harmonization of Technical Requirements for Pharmaceuticals for Human Use (ICH). The ICH Q3B presents general impurities guidelines based on daily dosage. The acceptance criteria for the impurities may be raised or lowered based on the degree of toxicity of the specific substance.

Donepezil, an acetylcholinesterase inhibitor, was developed for the purpose of treating Alzheimer's disease. It is commercially available as ARICEPT® oral tablets. Donepezil can be decomposed by heat, light, or moisture and generate various related substances (impurities). Therefore, the U.S. Pharmacopoeia has certain standard on impurities for donepezil-containing tablets, and prohibits the use of donepezil tablets that exceed the maximum impurities limit.

Impurities generated from decomposition of a principal component substance is generally evaluated using liquid chromatography. The analytical conditions (e.g. columns, mobile phase conditions, absorption wavelength) determine the kinds of impurities that can be analyzed. The U.S. Pharmacopoeia presents two methods for analyzing donepezil for impurities.

The first method (hereinafter referred to as "Procedure 1") can be used to detect desbenzyl donepezil, donepezil open ring, and donepezil N-oxide. The U.S. Pharmacopoeia recommends that each of these impurities be under 0.5%, and other unknown impurities under 0.2%.

The second method ("Procedure 2") can be used to detect desbenzyl, donepezil, donepezil pyridine analog, donepezil quaternary salt, donepezil indene analog, and deoxydonepezil. The U.S. Pharmacopoeia recommends that each of these five impurities be under 0.15%, other unknown impurities under 0.1%, and total impurities under 1.0%. Procedure 2 is advised if there is a possibility that a donepezil preparation may contain any of the five above-mentioned impurities.

However, oral preparations containing donepezil have been known to cause various side effects such as nausea, vomiting, and diarrhea due to a rapid rise in blood concentration. Another known issue with oral donepezil preparations is that they are not easy to take for elderly patients with compromised swallowing ability. To overcome these disadvantages, various research and developments efforts have been made in Korea and around the world on percutaneous absorption preparations containing donepezil. Most of this kind of research focuses on improving the skin permeability (which is very low) of donepezil-containing percutaneous preparations. Efforts to improve the stability of donepezil are disclosed in the U.S. Pat. No. 6,372,760, the Korea Patent Registration No. 10-0866720, the Korea Patent Registration No. 10-1408500, and Korea Patent Registration No. 10-1408454.

The U.S. Pat. No. 6,372,760 tried to improve the stability of donepezil by adding an organic acid. The Korea Patent Registration No. 10-0866720 relates to a method for improving the stability of donepezil by adding a high molecular weight acidic substance and a high molecular weight basic substance for oral preparations and syrups. However, it does not teach the application of a stabilizer for a percutaneous preparation.

Also, Korea Patent Registration No. 10-1408500 and 10-1408454 disclose methods of inhibiting the formation of donepezil impurities in percutaneous absorption preparations using a combination of two stabilizers selected from the group consisting of isoascorbic acid, 2-mercaptobenzimidazole, hydroxymethanesulfonic acid metal salt, rutin, 2,6-di-t-butyl-4-methylphenol, ascorbic acid and metabisulfite metal salt thereof. According to the prior art literature referenced above, a single stabilizer cannot effectively inhibit the two types of impurities (donepezil N-oxide and desbenzyl donepezil) and total impurities. The above-mentioned prior art teaches that the use of a combination of two types of stabilizers can successfully inhibit the two types of impurities (donepezil N-oxide and desbenzyl donepezil) and total impurities. However, the evaluation of impurities was conducted using only one of the two procedures taught by the U.S. Pharmacopoeia. Therefore, it is difficult to say that it effectively suppressed all the various potential impurities produced from donepezil.

The present inventors, while studying percutaneous preparation containing donepezil, discovered that the use of monothioglycerol, thiocyanate metal salt (preferably, potassium salt) or dimethylthiourea as a single stabilizer can effectively inhibit all the various types of impurities generated as a result of the decomposition of donepezil, culminating in the completion of the present invention.

DISCLOSURE

Technical Problem

The object of the present invention is to provide a stable percutaneous preparation comprising donepezil by reducing the formation of impurities of donepezil.

Technical Solution

To accomplish the above-mentioned objective, the present invention provides a donepezil-containing percutaneous absorption preparation for the treatment of dementia comprising a support layer, a drug-containing layer, and a release layer, wherein the drug-containing layer comprises donepezil or a pharmaceutically acceptable salt thereof as an active ingredient; monothioglycerol, thiocyanate metal salt (preferably potassium salt) or dimethylthiourea as a stabilizer; and a pressure-sensitive adhesive.

The present invention is further described below.

Donepezil is an acetylcholinesterase inhibitor and may be used in its free base form or as a pharmaceutically acceptable salt thereof. Among the pharmaceutically acceptable salts of donepezil, acid addition salts formed by pharmaceutically acceptable free acid are useful. Preferable acid addition salts are derived from inorganic acids such as hydrochloric acid, nitric acid, phosphoric acid, sulfuric acid, hydrobromic acid, nitrous acid, and phosphorous acid, or from non-toxic organic acids such as aliphatic mono- and di-carboxylates, phenyl-substituted alkanoates, hydroxyalkanoates, hydroxyalkanedioates, aromatic acids, aliphatic and aromatic sulfonic acids. Such pharmaceutically non-toxic salts include sulfate, pyrosulfate, bisulfate, sulfite, bisulfite, nitrate, phosphate, monohydrogen phosphate, dihydrogenphosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butene-1,4-dioate, hexane-1,6-dioate, benzoate, chlorobenzoate, methyl benzoate, dinitrobenzoate, hydroxybenzoate, methoxybenzoate, phthalate, terephthalate, benzenesulfonate, toleuenesulfonate, chlorobenzenesulfonate, xylene sulfonate, phenyl acetate, phenyl propionate, phenylbutyrate, citrate, lactate, β-hydroxybutyrate, glycolate, malate, tartrate, methanesulfonate, propanesulfonate, naphthalene-1-sulfonate, naphthalene-2-sulfonate, and mandelate.

In terms of dispersibility and percutaneous absorbability, donepezil in the form of a free base may be preferable in the drug-containing layer. Although no particular limit is imposed on the concentration of donepezil in the percutaneous absorption preparation of the present, for better dispersion and percutaneous absorption of donepezil from the drug-containing layer, preferred content range of donepezil is 1-20 wt % (of the weight of the drug-containing layer), preferably 1.5-15 wt %, and more preferably 2-10 wt %.

A "stabilizer" in the present invention is monothioglycerol, thiocyanate metal salt (preferably, potassium salt), or dimethylthiourea. One or more stabilizers may be used.

The stabilizer is contained in the drug-containing layer, and no particular limit is imposed on the weight percentage of the stabilizer so long as it does not adversely affect the physical properties of the drug-containing layer. In determining a preferable example of the upper limit of the stabilizer ratio, per weight of the drug-containing layer (i.e., the total weight of the solid content of the combination used in forming the drug-containing layer), a few factors were considered. At above 5 wt %, the physical properties of the drug-containing layer such as adhesiveness may be compromised. At below 0.005 wt %, sufficient stabilizing effect may not be achieved. Therefore, the preferable range of weight percentage of the stabilizer is from 0.0005 wt % to 5 wt %, preferably from 0.005 wt % to 3 wt %, and more preferably from 0.05 wt % to 2 wt %. The drug-containing layer may further comprise a known stabilizer.

A pressure-sensitive adhesive in the present invention is not particularly limited. Examples include acrylic pressure-sensitive adhesive; rubber-based pressure-sensitive adhesives such as silicone, polyisoprene, styrene-butadiene, styrene-isoprene-styrene block copolymer; silicone adhesive; and vinyl-based polymeric adhesives such as polyvinyl alcohol, polyvinyl alkyl ether, and poly(vinyl acetate).

A more preferable example of pressure-sensitive adhesives in the present invention is styrene-isoprene-styrene block copolymer. Styrene-isoprene-styren block copolymer properties vary widely depending on styrene content, diblock content, melting point, and solution viscosity.

Styrene-isoprene-styrene block copolymer used in the present invention is not particularly limited. Preferably, its solution viscosity is above 0.5 Pa*s, preferably 0.7 Pa*s, and more preferably 0.9 Pa*s, as measured according to "Method of measuring viscosity of styrene-isoprene-styrene block copolymer" described in the 2013 edition of the Japanese Pharmaceutical Excipients. The upper limit of the solution viscosity is not particularly limited, but preferably it is below 2.0 Pa*s, and more preferably 1.8 Pa*s.

If the drug-containing layer does not contain sufficient amount of pressure-sensitive adhesive, the drug-containing layer may not be able to maintain its shape. If too much adhesive is used, the skin permeability of the drug is reduced. Therefore, the adhesive content of the drug-containing layer of the present invention is preferably from 10 wt % to 70 wt %, more preferably 15 wt %-65 wt %, even more preferably 20 wt %-60 wt %, and still more preferably 25 wt %-55 wt %.

The pressure-sensitive adhesive composition in the percutaneous absorption formulation may contain a plasticizer. Examples of plasticizers that can be used in the present invention include but are not limited to paraffinic process oils, naphthenic process oils, aromatic process oils, olive oil, camellia oil, tall oil, castor oil, isopropyl myristate, hexyl laurate, mineral oil, octyldodecyl myristate, prolylene glycol, and propylene glycol monocaprylate. A combination of two or more of the aforementioned platicizers may be used. The amount of the plasticizers to be incorporated is preferably from 10 wt % to 80 wt % in order to maintain sufficient cohesive strength of the percutaneous absorption preparation. More preferably, it is 20 wt %-75 wt %, more preferably 25 wt %-70 wt %, and even more preferably 30 wt %-65 wt %.

A tackifying resin may be added to the drug-containing layer of the present invention in order to adjust the adhesiveness of the percutaneous absorption preparation. Tackifying resins that can be used in the present invention include but are not limited to rosin derivatives, alicyclic saturated hydrocarbon resin, and aliphatic hydrocarbon resin. Although terpene resin was used in the examples of the present invention, it is not intended to be construed as limiting the scope of the present invention.

If a tackifier is included in the drug-containing layer, the content of the tackifier is preferably at or below 20 wt % in order to reduce skin irritation. More preferably it is below 15 wt %, more preferably 10 wt %, and even more preferably 8 wt %. No tackifier at all is most preferred. That is, in terms of skin adhesiveness of the patch, the content of the tackifier may be adjusted depending on the blending ratio of donepezil, styrene-isoprene-styrene block copolymer, solubilizer, and plasticizer in the drug-containing layer. A tackifier may not be needed at all if sufficient skin adhesion is achieved without a tackifier.

No particular limit is imposed on the method of preparing the percutaneous absorption preparation. Conventional methods of preparing a percutaneous absorption preparation, such as that described in the Korean Pharmacopoeia—that is, dissolving or dispersing a pressure-sensitive adhesive agent, donepezil, a stabilizer, and a plasticizer; applying the solution or dispersion onto the surface of the release layer; drying; and laminating support onto it.

One embodiment example of the present invention is a method of producing a donepezil percutaneous absorption preparation comprising the following steps:
  i) dissolving donepezil and monothioglycerol, thiocyanate metal salt or dimethylthiourea in an organic solvent;
  ii) applying the solution obtained in (i) onto the release layer an drying it to form a drug-containing layer; and iii) laminating the drug-containing layer obtained in (ii) with the support layer.

Examples of possible solvents that can be used in the above-mentioned method according to the present invention include ethyl acetate, toluene, hexane, 2-propanol, methanol, ethanol, methylene chloride, and tetrahydrofuran. The temperature at which the adhesive is dissolved or dispersed in the solvent is not particularly limited. However, higher temperatures may increase the likelihood of solvent evaporation and may increase decomposition of donepezil causing formation of more impurities. Therefore, the preferred temperature range is at or below 80° C., and more preferably at or below 60° C.

Furthermore, the method above of applying the solution or dispersion to the release layer, drying it, and laminating the support for the present invention may follow conventional methods of preparing percutaneous absorption preparation.

Advantageous Effects

The present invention provides a percutaneous absorption preparation of donepezil that is highly stable by inhibiting decomposition of donepezil and thereby reducing formation of impurities.

DESCRIPTION OF EMBODIMENTS

The present invention is further described below with examples and experimental examples. The examples and experimental examples provided below are provided to further describe the present invention in detail to a skilled person and shall not be construed as limiting the scope of the present invention.

<Examples 1 Through 3> Percutaneous Absorption Preparation According to the Present Invention Dissolve 16 g of styrene-isoprene-styrene block copolymer, 4.7 g of octyldodecyl myristate, 3 g of terpene resin, 6.5 g of propylene glycol monocaprylate, and 1.3 g of donepezil in 27 g of ethyl acetate to obtain an ethyl acetate solution comprising donepezil. Then, dissolve 0.13 g of the stabilizer specified in Table 1 in 1 g of methanol and mix it with the ethyl acetate solution from the previous step. Apply this mixture onto a silicone-coated PET film and dry it for 30 minutes in an oven at 80° C. Afterwards, laminate it with a backing film. The obtained results are Examples 1 through 3 of the present invention.

TABLE 1

| Example No. | Stabilizer |
| --- | --- |
| Example 1 | monothioglycerol |
| Example 2 | potassium thiocyanate |
| Example 3 | dimethylthiourea |

<Comparative Example 1> Percutaneous Absorption Preparation without Stabilizer

Comparative example 1 is a percutaneous absorption preparation that is identical to example 1 in composition and method of preparation except that it does not contain a stabilizer.

<Comparative Example 2> Percutaneous Absorption Preparation with Citric Acid as Stabilizer Comparative example 2 is a percutaneous absorption preparation that is identical to example 1 in composition and method of preparation except that it contains citric acid as stabilizer. Citric acid was selected from the stabilizers disclosed in U.S. Pat. No. 6,372,760.

<Comparative Examples 3 Through 15> Percutaneous Absorption Preparations with Various Stabilizers Comparative examples 3 through 15 are percutaneous absorption preparations prepared according to the same composition and preparation method as example 1, with the addition of various known stabilizers as specified in Table 2 below.

TABLE 2

| | Stabilizer |
| --- | --- |
| Comparative Example 3 | Cysteine |
| Comparative Example 4 | Tryptophan |
| Comparative Example 5 | Thiomalic acid |
| Comparative Example 6 | Catechin |
| Comparative Example 7 | Sodium thiosulfate |
| Comparative Example 8 | Dibutylhydroxytoluene |
| Comparative Example 9 | Butylhydroxyanisole |
| Comparative Example 10 | Rutin |
| Comparative Example 11 | Ascorbic acid |
| Comparative Example 12 | Isoascorbic acid |
| Comparative Example 13 | 2,6-di-t-butyl-4-methylphenol |
| Comparative Example 14 | 2-mercaptobenzimidazole |
| Comparative Example 15 | Sodium metabisulfite |

<Comparative Examples 16 Through 19> Percutaneous Absorption Preparation with Two Stabilizers Four pairs of stabilizers were selected from the group of stabilizers disclosed in the Korea Patent Registration No. 10-1408500 that most effectively inhibited the formation of donepezil N-oxide, desbenzyl donepezil, and total impurities.

Percutaneous absorption preparations were prepared according to the same composition and preparation method as example 1, with the addition of two stabilizers (0.13 g for each stabilizer) as specified in Table 3 below. The resulting preparations were labeled as comparative examples 16 through 19.

TABLE 3

| | Stabilizers |
| --- | --- |
| Comparative Example 16 | isoascorbic acid/2-mercaptobenzimidazole |
| Comparative Example 17 | 2-mercaptobenzimidazole/2,6-di-t-butyl-4-methylphenol |
| Comparative Example 18 | 2-mercaptobenzimidazole/Rutin |
| Comparative Example 19 | 2,6-di-t-butyl-4-methylphenol/Sodium hydroxymethanesulfonate |

<Comparative Example 20> Percutaneous Absorption Preparation with Two Stabilizers A percutaneous absorption preparation was prepared according to the same composition and preparation method as example 1, with the addition of ascorbic acid and sodium metabisulfite (0.13 g of each), which are stabilizers disclosed in Korea Patent Registration No. 10-1408454. The resulting preparation was labeled as comparative example 20.

<Experimental Example 1> Impurities Testing with Procedure 1 after 48 Hours of Storage at 70° C.

Percutaneous absorption preparations of examples and comparative examples were tested for donepezil impurities according to Procedure 1 as below, after 48 hours of storage at 70° C.

1. Impurities Analysis by Procedure 1

Each percutaneous absorption preparation was dissolved in ethyl acetate. Methanol was added and the resulting solution was stirred for 30 minutes and centrifuged for 5 minutes. The resulting supernatant was used as the sample solution for Procedure 1 of the U.S. Pharmacopoeia. The standard solution was prepared so that the concentration of donepezil hydrochloride standard was 0.8 ug/mL using a solvent mixture of ethyl acetate:methanol=15:85 (volume ratio).

<Procedure 1: Liquid Chromatography Conditions>
- Column: Inertsil octadecylsilane-2 (4.6×150 mm, C18, 5 um)
- Mobile phase: Dissolve 2.5 g of Sodium 1-decanesulfonate 2.5 g in 650 mL of purified water. Then, add 1 mL of 70% perchloric acid solution and 350 mL of acetonitrile.
- Column temperature: 35° C.
- Flow rate: 1.4 mL/min
- Injection size: 20 uL
- UV absorptiometer: 271 nm
- Calculation:

Impurity %=$(Ru/Rs) \times (Cs/Cu) \times (1/F) \times 100$

- Ru: peak response of any individual impurity from the sample solution
- Rs: peak response of donepezil from the standard solution
- Cs: concentration in the standard solution (mg/mL)
- Cu: concentration in the sample solution (mg/mL)
- F: relative correction factor for each impurity 2. Impurities Analysis by Procedure 1 after 48 Hours of Storage at 70° C.

The percutaneous absorption preparations of the examples according to the present invention and comparative examples were stored for 48 hours at 70° C., and then tested for impurities according to Procedure 1. The results are shown in Table 4.

As seen in Table 4 below, a lot of decomposition of donepezil was observed in comparative example 1 without stabilizer, at the relative retention times (RRT) 0.53 (unidentified impurity), 0.7 (donepezil open ring), and 1.2 (donepezil N-oxide), as well as for total impurities—demonstrating the need for stabilizers in percutaneous absorption preparations of donepezil.

Comparative example 2, which used citric acid (an organic acid disclosed in the U.S. Pat. No. 6,372,760), did not meet the criteria presented by the U.S. Pharmacopoeia at the relative retention time (RRT) 1.2 (donepezil N-oxide).

As for comparative examples 3 through 15, which are percutaneous absorption preparations with known stabilizers, comparative example 3 (cysteine), comparative example 5 (thiomalic acid), comparative example 7 (sodium thiosulfate), and comparative example 14 (2-mercaptobenzimidazole) did meet the criteria in the U.S. Pharmacopoeia. However, comparative example 6 (catechin), comparative example 11 (ascorbic acid), comparative example 12 (isoascorbic acid), and comparative example 15 (Sodium metabisulfite) produced excessive impurity at RTT 1.2 (Donepezil N-oxide), and comparative example 4 (tryptophan) and comparative example 10 (Rutin) did not meet the criteria for for 1.2 (donepezil N-oxide) like comparative example 2. Comparative example 8 (Dibutylhydroxytoluene), comparative example 9 (Butylhydroxyanisole), and comparative example 13 (2,6-di-t-butyl-4-methylphenol) did not meet the criteria for most of the impurities as well as for total impurities.

Comparative example 16 (ascorbic acid/2-mercaptobenzimidazole), comparative example 17 (2-mercaptobenzimidazole/2,6-di-t-butyl-4-methylphenol), comparative example 18 (2-mercaptobenzimidazole/rutin), comparative example 19 (2,6-di-t-butyl-4-methylphenol/sodium hydroxymethanesulfonate) and comparative example 20 (ascorbic acid/sodium metabisulfite), which used a combination of two stabilizers selected from the stabilizers disclosed in Korea Patent Registration No. 10-1408500 and Korea Patent Registration No. 10-1408454, met the U.S. Pharmacopoeia criteria for all RRT except comparative example 19 for RRT 0.48 (unidentified impurity).

In contrast, examples 1 through 3 according to the present invention met the criteria presented in the U.S. Pharmacopoeia despite containing only one stabilizer each, demonstrating the outstanding stabilizing effect of monothioglycerol, thiocyanate metal salt (preferably potassium salt) or dimethylthiourea.

| Impurity | Relative retention time (RRT) | Relative correction factor (F) | Acceptance criteria (%) |
|---|---|---|---|
| Desbenzyl donepezil | 0.33 | 1 | 0.5 |
| Donepezil open ring | 0.7 | 0.6 | 0.5 |
| Donepezil N-oxide | 1.2 | 1 | 0.5 |
| Any individual unspecified degradation product | — | — | 0.2 |

TABLE 4

| | | Content (%) of each impurity (RRT) | | | | | |
|---|---|---|---|---|---|---|---|
| | Stabilizer | RRT0.33[1] | RRT0.48[2] | RRT0.53[3] | RRT0.7[4] | RRT1.2[5] | Total |
| Example 1 | monothioglycerol | 0.01 | 0.00 | 0.06 | 0.04 | 0.26 | 0.39 |
| Example 2 | potassium thiocyanate | 0.01 | 0.05 | 0.17 | 0.12 | 0.00 | 0.40 |
| Example 3 | dimethylthiourea | 0.02 | 0.08 | 0.04 | 0.04 | 0.00 | 0.33 |
| Comparative Example 1 | — | 0.02 | 0.00 | 0.27 | 0.25 | 1.27 | 1.94 |
| Comparative Example 2 | citric acid | 0.01 | 0.00 | 0.11 | 0.05 | 0.83 | 1.03 |
| Comparative Example 3 | cysteine | 0.00 | 0.00 | 0.08 | 0.08 | 0.31 | 0.51 |
| Comparative Example 4 | tryptophan | 0.03 | 0.00 | 0.15 | 0.09 | 0.95 | 1.27 |
| Comparative Example 5 | thiomalic acid | 0.05 | 0.00 | 0.12 | 0.07 | 0.25 | 0.78 |
| Comparative Example 6 | catechin | 0.01 | 0.00 | 0.04 | 0.06 | 0.67 | 0.77 |
| Comparative Example 7 | sodium thiosulfate | 0.01 | 0.00 | 0.13 | 0.11 | 0.27 | 0.57 |
| Comparative Example 8 | dibutylhydroxytoluene | 0.02 | 0.00 | 0.39 | 0.40 | 1.24 | 2.13 |
| Comparative Example 9 | butylhydroxyanisole | 0.03 | 0.00 | 1.24 | 2.68 | 3.04 | 7.29 |
| Comparative Example 10 | rutin | 0.01 | 0.00 | 0.17 | 0.07 | 0.84 | 1.12 |
| Comparative Example 11 | ascorbic acid | 0.01 | 0.00 | 0.01 | 0.04 | 0.79 | 0.92 |
| Comparative Example 12 | isoascorbic acid | 0.01 | 0.00 | 0.01 | 0.05 | 0.85 | 0.95 |
| Comparative Example 13 | 2,6-di-t-butyl-4-methylphenol | 0.01 | 0.00 | 0.38 | 0.42 | 1.27 | 2.19 |
| Comparative Example 14 | 2-mercaptobenzimidazole | 0.01 | 0.00 | 0.11 | 0.05 | 0.00 | 0.21 |
| Comparative Example 15 | sodium metabisulfite | 0.01 | 0.00 | 0.10 | 0.10 | 0.51 | 0.82 |
| Comparative Example 16 | isoascorbic acid/ 2-mercaptobenzimidazole | 0.01 | 0.00 | 0.12 | 0.06 | 0.00 | 0.23 |
| Comparative Example 17 | 2-mercaptobenzimidazole/ 2,6-di-t-butyl-4-methylphenol | 0.01 | 0.00 | 0.17 | 0.03 | 0.00 | 0.25 |
| Comparative Example 18 | 2-mercaptobenzimidazole/rutin | 0.01 | 0.15 | 0.09 | 0.07 | 0.00 | 0.44 |
| Comparative Example 19 | 2,6-di-t-butyl-4-methylphenol/ Sodium hydroxymethanesulfonate | 0.01 | 0.25 | 0.00 | 0.04 | 0.14 | 0.46 |
| Comparative Example 20 | ascorbic acid/sodium metabisulfite | 0.01 | 0.00 | 0.01 | 0.05 | 0.49 | 0.62 |

[1]RRT 0.33: Desbenzyldonepezil, within 0.5%
[2]RRT 0.48: Unidentified impurity, within 0.2%
[3]RRT 0.53: Unidentified impurity, within 0.2%
[4]RRT 0.7: Donepezil open ring, within? 0.5%
[5]RRT 1.2: Donepezil N-oxdie, within? 0.5%

<Experimental Example 2> Impurities Analysis by Procedure 2 after 48 Hours of Storage at 70° C.

To test for donepezil impurities, percutaneous absorption preparation of the examples and comparative examples were stored for 48 hours at 70° C. and analyzed for impurities according to Procedure 2 as described below.

1. Impurities Analysis by Procedure 2

Each percutaneous absorption preparation was dissolved in ethyl acetate. Then, a solution mixture of 0.1 N hydrochloric acid and methanol at a 25:75 ratio was added and the resulting mixture was stirred for 30 minutes and centrifuged for 5 minutes. The resulting supernatant was used as the sample solution for Procedure 2 of the U.S. Pharmacopoeia. The standard solution was prepare so that the concentration of donepezil hydrochloride standard was 10 ug/mL using a solvent mixture of ethyl acetate:methanol:0.1 N hydrochloric acid=100:675:225 (volume ratio).

<Procedure 2: Liquid Chromatography Conditions>

Column: CAPCELLPAK™ (4.6×250 mm, C18.5 um)

Mobile phase A: Add 1 mL of phosphoric acid in 1 L of purified water. Adjust with triethylamine to a pH of 6.5. Pass through a filter, remove bubbles, and use as mobile phase.

| Mobile phase B: acetonitrile | | |
|---|---|---|
| Time (mm) | Mobile phase A (%) | Mobile phase B (%) |
| 0 | 75 | 25 |
| 10 | 40 | 60 |
| 40 | 40 | 60 |
| 41 | 75 | 25 |
| 50 | 75 | 25 |

Column temperature: 50° C.
Flow rate: 1.5 mL/min
Injection size: 20 uL
UV absorptiometer: 286 nm
Calculation:

Impurity %=$(Ru/Rs) \times (Cs/Cu) \times (1/F) \times 100$

Ru: peak response of any individual impurity from the sample solution
Rs: peak response of donepezil from the standard solution
Cs: concentration in the standard solution (mg/mL)
Cu: concentration in the sample solution (mg/mL)
F: relative correction factor for each impurity 2. Impurities Analysis by Procedure 2 after 48 Hours of Storage at 70° C.

The percutaneous absorption preparations of the examples according to the present invention and comparative examples were stored for 48 hours at 70° C., and then tested for impurities according to Procedure 2. The results are shown in Table 5.

As seen in Table 5 below, a lot of decomposition of donepezil was observed in comparative example 1 without a stabilizer with Procedure 2, at relative retention times (RRT) 0.49 (donepezil pyridine analog), 0.57 (unidentified impurity), and total impurities—demonstrating the need for stabilizers in percutaneous absorption preparations of donepezil.

As for comparative example 2, which used citric acid (an organic acid disclosed in the U.S. Pat. No. 6,372,760), the RTT 0.49 (donepezil pyridine analog) and 0.57 (unidentified impurity) did not meet the criteria presented by the U.S. Pharmacopoeia.

Unlike with Procedure 1, none of comparative examples 3 through 15, which are percutaneous absorption preparations with known stabilizers met the criteria of the U.S. Pharmacopoeia at all with Procedure 2. That is, comparative example 6 (catechin), comparative example 11 (ascorbic acid) and comparative example 12 (isoascorbic acid) produced excess impurity at RRT 0.49 (donepezil pyridine analog). Comparative example 5 (thiomalic acid) and comparative example 7 (sodium thiosulfate) produced excess impurity at RRT 0.57 (unidentified impurity). Comparative example 8 (dibutylhydroxytoluene), comparative example 9 (butylhydroxyanisole), comparative example 13 (2,6-di-t-butyl-4-methylphenol) and comparative example 14 (2-mercaptobenzimidazole) did not meet the criteria for 1-3 impurities as well as total impurities.

Comparative example 16 (ascorbic acid/2-mercaptobenzimidazole), comparative example 17 (2-mercaptobenzimidazole/2,6-di-t-butyl-4-methylphenol), comparative example 18 (2-mercaptobenzimidazole/Rutin) and comparative example 19 (2,6-di-t-butyl-4-methylphenol/Sodium hydroxymethanesulfonate), which used a combination of two stabilizers selected from the stabilizers disclosed in Korea Patent Registration No 10-1408500, did not meet the U.S. Pharmacopoeia criteria. Comparative examples 16 through 18 also failed to meet the criteria for total impurities.

Comparative example 20 (ascorbic acid/Sodium metabisulfite), which used a combination of two stabilizers selected from the stabilizers disclosed in Korea Patent Registration No. 10-140854, did not meet the U.S. Pharmacopoeia criteria for RRT 0.49 (donepezil pyridine analog).

| Impurity | Relative retention time (RRT) | Relative correction factor (F) | Acceptance criteria (%) |
|---|---|---|---|
| Desbenzyl donepezil | 0.23 | 1.5 | 0.15 |
| Donepezil pyridine analog | 0.49 | 1.9 | 0.15 |
| Donepezil quaternary salt | 0.68 | 0.74 | 0.15 |
| Donepezil indene analog | 1.7 | 2.2 | 0.15 |
| Deoxydonepezil | 2.1 | 1.3 | 0.15 |
| Any individual degradation product | — | 1.0 | 0.1 |
| Total impurities | — | — | 1.0 |

In contrast, examples 1 through 3 according to the present invention successfully met the criteria presented in the U.S. Pharmacopoeia despite each containing only one stabilizer—thus demonstrating the outstanding stabilizing effect of monothioglycerol, thiocyanate metal salt (preferably potassium salt) or dimethylthiourea.

TABLE 5

70° C., 48 hr, Procedure 2 of impurities analysis

| | | Content (%) of each impurity (RRT) | | | | | | | |
|---|---|---|---|---|---|---|---|---|---|
| | Stabilizer | RRT 0.23[1] | RRT 0.49[2] | RRT 0.57[3] | RRT 0.68[4] | RRT 1.03[5] | RRT 1.7[6] | RRT 2.1[7] | TOTAL |
| Example 1 | monothioglycerol | 0.11 | 0.12 | 0.08 | 0.00 | 0.00 | 0.00 | 0.00 | 0.53 |
| Example 2 | potassium thiocyanate | 0.02 | 0.00 | 0.08 | 0.02 | 0.00 | 0.00 | 0.00 | 0.56 |
| Example 3 | dimethylthiourea | 0.05 | 0.02 | 0.06 | 0.00 | 0.00 | 0.00 | 0.00 | 0.49 |
| Comparative Example 1 | — | 0.07 | 0.69 | 0.43 | 0.08 | 0.00 | 0.00 | 0.00 | 1.62 |
| Comparative Example 2 | citric acid | 0.01 | 0.44 | 0.16 | 0.02 | 0.00 | 0.00 | 0.00 | 0.71 |
| Comparative Example 3 | cysteine | 0.01 | 0.24 | 0.13 | 0.00 | 0.00 | 0.00 | 0.00 | 0.40 |
| Comparative Example 4 | tryptophan | 0.02 | 0.50 | 0.24 | 0.02 | 0.00 | 0.00 | 0.00 | 0.89 |
| Comparative Example 5 | thiomalic acid | 0.12 | 0.14 | 0.18 | 0.05 | 0.00 | 0.00 | 0.00 | 0.80 |
| Comparative Example 6 | catechin | 0.02 | 0.38 | 0.06 | 0.00 | 0.00 | 0.00 | 0.00 | 0.52 |
| Comparative Example 7 | sodium thiosulfate | 0.02 | 0.14 | 0.18 | 0.02 | 0.00 | 0.00 | 0.00 | 0.48 |
| Comparative Example 8 | Dibutylhydroxytoluene | 0.10 | 0.60 | 0.60 | 0.04 | 0.00 | 0.00 | 0.00 | 1.76 |
| Comparative Example 9 | Butylhydroxyanisole | 0.62 | 0.83 | 1.88 | 0.04 | 0.00 | 0.00 | 0.00 | 3.75 |
| Comparative Example 10 | Rutin | 0.01 | 0.46 | 0.26 | 0.02 | 0.00 | 0.00 | 0.00 | 0.88 |
| Comparative Example 11 | ascorbic acid | 0.02 | 0.45 | 0.01 | 0.02 | 0.00 | 0.00 | 0.00 | 0.59 |
| Comparative Example 12 | isoascorbic acid | 0.01 | 0.47 | 0.01 | 0.00 | 0.00 | 0.00 | 0.00 | 0.56 |
| Comparative Example 13 | 2,6-di-t-butyl-4-methylphenol | 0.09 | 0.59 | 0.58 | 0.00 | 0.00 | 0.00 | 0.00 | 1.62 |
| Comparative Example 14 | 2-mercaptobenzimidazole | 0.00 | 0.00 | 0.17 | 0.11 | 5.60 | 0.00 | 0.00 | 6.19 |
| Comparative Example 15 | Sodium metabisulfite | 0.03 | 0.27 | 0.17 | 0.03 | 0.00 | 0.00 | 0.00 | 0.70 |
| Comparative Example 16 | 2-isoascorbic acid/ mercaptobenzimidazole | 0.00 | 0.01 | 0.17 | 0.10 | 5.83 | 0.00 | 0.00 | 6.45 |
| Comparative Example 17 | 2-mercaptobenzimidazole/ 2,6-d i-t-buty1-4-methylphenol | 0.00 | 0.01 | 0.25 | 0.06 | 5.40 | 0.00 | 0.00 | 5.98 |
| Comparative Example 18 | 2-mercaptobenzimidazole/ Rutin | 0.00 | 0.00 | 0.31 | 0.11 | 3.52 | 0.00 | 0.00 | 4.37 |
| Comparative Example 19 | 2,6-di-t-butyl-4-methylphenol/Sodium hydroxymethanesulfonate | 0.00 | 0.11 | 0.28 | 0.00 | 0.00 | 0.00 | 0.00 | 0.48 |
| Comparative Example 20 | ascorbic acid/ Sodium metabisulfite | 0.01 | 0.39 | 0.00 | 0.01 | 0.00 | 0.00 | 0.00 | 0.51 |

[1] RRT 0.23: Desbenzyldonepezil, within 0.15%
[2] RRT 0.49: Donepezil pyridine analog, within 0.15%
[3] RRT 0.57: Unidentified impurity, within 0.1%
[4] RRT 0.68: Donepezil quaternary salt, within 0.15%
[5] RRT 1.03: Unidentified impurity, within 0.1%
[6] RRT 1.7: Donepezil indene analog, within 0.15%
[7] RRT 2.1: Deoxydonepezil, within 0.15%

<Experimental Example 3> Impurities Analysis by Procedures 1 and 2 after 24 Hours of Storage at 80° C.

Percutaneous absorption preparations of examples and comparative examples were tested for donepezil impurities according to Procedure 1 and Procedure 2 after 24 hours of storage at 80° C.

1. Impurities Analysis by Procedure 1 after 24 Hours of Storage at 80° C.

TABLE 6

| | | 80° C., 24 hr, Procedure 1 ||||||
| | | Content (%) of each impurity (RRT) ||||||
| | stabilizer | RRT0.33[1] | RRT0.48[2] | RRT0.53[3] | RRT0.7[4] | RRT1.2[5] | Total |
|---|---|---|---|---|---|---|---|
| Example 1 | monothioglycerol | 0.02 | 0.00 | 0.05 | 0.06 | 0.09 | 0.24 |
| Example 2 | potassium thiocyanate | 0.00 | 0.03 | 0.14 | 0.02 | 0.00 | 0.22 |
| Example 3 | dimethylthiourea | 0.03 | 0.09 | 0.06 | 0.04 | 0.00 | 0.24 |
| Comparative Example 1 | — | 0.03 | 0.00 | 0.19 | 0.22 | 1.00 | 1.62 |
| Comparative Example 2 | citric acid | 0.01 | 0.00 | 0.09 | 0.05 | 0.65 | 0.83 |
| Comparative Example 3 | cysteine | 0.02 | 0.00 | 0.06 | 0.06 | 0.18 | 0.35 |
| Comparative Example 4 | tryptophan | 0.02 | 0.00 | 0.12 | 0.07 | 0.78 | 1.00 |
| Comparative Example 5 | thiomalic acid | 0.04 | 0.00 | 0.11 | 0.04 | 0.15 | 0.57 |
| Comparative Example 6 | catechin | 0.01 | 0.00 | 0.05 | 0.05 | 0.41 | 0.52 |
| Comparative Example 7 | sodium thiosulfate | 0.04 | 0.00 | 0.13 | 0.11 | 0.44 | 0.77 |
| Comparative Example 8 | Dibutylhydroxytoluene | 0.02 | 0.00 | 0.37 | 0.48 | 1.12 | 2.08 |
| Comparative Example 9 | Butylhydroxyanisole | 0.03 | 0.00 | 1.34 | 2.90 | 3.25 | 8.26 |
| Comparative Example 10 | Rutin | 0.01 | 0.00 | 0.14 | 0.05 | 0.59 | 0.87 |
| Comparative Example 11 | ascorbic acid | 0.01 | 0.00 | 0.00 | 0.04 | 0.50 | 0.62 |
| Comparative Example 12 | isoascorbic acid | 0.01 | 0.00 | 0.00 | 0.05 | 0.69 | 0.80 |
| Comparative Example 13 | 2,6-di-t-butyl-4-methylphenol | 0.01 | 0.00 | 0.33 | 0.46 | 1.02 | 2.00 |
| Comparative Example 14 | 2-mercaptobenzimidazole | 0.02 | 0.00 | 0.09 | 0.08 | 0.00 | 0.25 |
| Comparative Example 15 | Sodium metabsulfitei | 0.01 | 0.00 | 0.52 | 0.11 | 0.52 | 0.95 |
| Comparative Example 16 | isoascorbic acid/ 2-mercaptobenzimidazole | 0.02 | 0.00 | 0.10 | 0.04 | 0.00 | 0.19 |
| Comparative Example 17 | 2-mercaptobenzimidazole/ 2,6-di-t-butyl-4-methylphenol | 0.02 | 0.00 | 0.16 | 0.07 | 0.00 | 0.29 |
| Comparative Example 18 | 2-mercaptobenzimidazole/ Rutin | 0.00 | 0.22 | 0.09 | 0.05 | 0.00 | 0.50 |
| Comparative Example 19 | 2,6-di-t-butyl-4-methylphenol/ Sodium hydroxymethanesulfonate | 0.01 | 0.23 | 0.00 | 0.05 | 0.13 | 0.51 |
| Comparative Example 20 | ascorbic acid/ Sodium metabisulfite | 0.01 | 0.00 | 0.01 | 0.05 | 0.48 | 0.77 |

[1]RRT 0.33: Desbenzyldonepezil, within 0.5%
[2]RRT 0.48: unidentified impurity, within 0.2%
[3]RRT 0.53: unidentified impurity, within 0.2%
[4]RRT 0.7: Donepezil open ring, within 0.5%
[5]RRT 1.2: Donepezil N-oxdie, within 0.5%

2. Impurities Analysis by Procedure 2 after 24 Hours of Storage at 80° C.

TABLE 7

80° C., 24 hr, Procedure 2

Content (%) of each impurity (RRT)

| | stabilizer | RRT 0.23[1] | RRT 0.49[2] | RRT 0.57[3] | RRT 0.68[4] | RRT 1.03[5] | RRT 1.7[6] | RRT 2.1[7] | TOTAL |
|---|---|---|---|---|---|---|---|---|---|
| Example 1 | monothioglycerol | 0.10 | 0.08 | 0.07 | 0.11 | 0.00 | 0.00 | 0.00 | 0.60 |
| Example 2 | potassium thiocyanate | 0.01 | 0.00 | 0.06 | 0.00 | 0.00 | 0.00 | 0.00 | 0.51 |
| Example 3 | dimethyl thiourea | 0.04 | 0.01 | 0.07 | 0.00 | 0.00 | 0.00 | 0.00 | 0.44 |
| Comparative Example 1 | — | 0.05 | 0.50 | 0.32 | 0.06 | 0.06 | 0.00 | 0.00 | 1.31 |
| Comparative Example 2 | citric acid | 0.01 | 0.36 | 0.14 | 0.00 | 0.00 | 0.00 | 0.00 | 0.59 |
| Comparative Example 3 | cysteine | 0.01 | 0.20 | 0.13 | 0.00 | 0.00 | 0.00 | 0.00 | 0.35 |
| Comparative Example 4 | tryptophan | 0.01 | 0.24 | 0.15 | 0.00 | 0.00 | 0.00 | 0.00 | 0.47 |
| Comparative Example 5 | thiomalic acid | 0.19 | 0.08 | 0.27 | 0.07 | 0.00 | 0.00 | 0.00 | 1.10 |
| Comparative Example 6 | catechin | 0.10 | 0.28 | 0.21 | 0.00 | 0.00 | 0.00 | 0.00 | 0.76 |
| Comparative Example 7 | sodium thiosulfate | 0.02 | 0.24 | 0.22 | 0.00 | 0.00 | 0.00 | 0.00 | 0.60 |
| Comparative Example 8 | Dibutylhydroxytoluene | 0.10 | 0.50 | 0.57 | 0.00 | 0.15 | 0.00 | 0.00 | 1.64 |
| Comparative Example 9 | Butylhydroxyanisole | 0.87 | 0.93 | 2.09 | 0.00 | 0.13 | 0.00 | 0.00 | 4.28 |
| Comparative Example 10 | Rutin | 0.03 | 0.24 | 0.30 | 0.00 | 0.00 | 0.00 | 0.00 | 0.61 |
| Comparative Example 11 | ascorbic acid | 0.00 | 0.30 | 0.03 | 0.00 | 0.00 | 0.00 | 0.00 | 0.45 |
| Comparative Example 12 | isoascorbic acid | 0.00 | 0.26 | 0.02 | 0.00 | 0.00 | 0.00 | 0.00 | 0.38 |
| Comparative Example 13 | 2,6-di-t-butyl-4-methyl phenol | 0.08 | 0.25 | 0.48 | 0.00 | 0.00 | 0.00 | 0.00 | 1.47 |
| Comparative Example 14 | 2-mercaptobenzimidazole | 0.00 | 0.00 | 0.10 | 0.05 | 4.97 | 0.00 | 0.00 | 5.72 |
| Comparative Example 15 | Sodium metabisulfite | 0.03 | 0.28 | 0.20 | 0.00 | 0.00 | 0.00 | 0.00 | 0.72 |
| Comparative Example 16 | isoascorbic acid/ 2-mercaptobenzimidazole | 0.01 | 0.06 | 0.09 | 0.24 | 4.21 | 0.00 | 0.00 | 5.24 |
| Comparative Example 17 | 2-mercaptobenzimidazole/ 2,6-di-t-butyl-4-methylphenol | 0.01 | 0.01 | 0.15 | 0.04 | 5.40 | 0.00 | 0.00 | 6.27 |
| Comparative Example 18 | 2-mercaptobenzimidazole/ Rutin | 0.01 | 0.00 | 0.23 | 0.03 | 3.31 | 0.00 | 0.00 | 4.67 |
| Comparative Example 19 | 2,6-di-t-butyl-4-methylphenol/Sodium hydroxymethanesulfonate | 0.05 | 0.11 | 0.17 | 0.00 | 0.00 | 0.00 | 0.00 | 0.42 |
| Comparative Example 20 | ascorbic acid/ Sodium metabisulfite | 0.00 | 0.21 | 0.00 | 0.00 | 0.00 | 0.00 | 0.00 | 0.30 |

[1] RRT 0.23: Desbenzyldonepezil, within 0.15%
[2] RRT 0.49: Donepezil pyridine analog, within 0.15%
[3] RRT 0.57: Unidentified impurity, within 0.1%
[4] RRT 0.68: Donepezil quaternary salt, within 0.15%
[5] RRT 1.03: Unidentified impurity, within 0.1%
[6] RRT 1.7: Donepezil indene analog, within 0.15%
[7] RRT 2.1: Deoxydonepezil, within 0.15%

As seen in Table 6 and Table 7 above, the impurity content result of experimental example 3 was similar to the result of experimental examples 1 and 2, even with differing conditions.

In the above results, only a subset of percutaneous absorption preparations of donepezil containing a previously known stabilizers were found to be acceptable according to Procedure 1, and none of them met the acceptance criteria of Procedure 2. Furthermore, comparative example 2, 16 through 20 (which are prior art examples) were mostly acceptable according to Procedure 1 but not acceptable according to Procedure 2.

In contrast, examples 1 through 3 according to the present invention met the acceptance criteria of both Procedure 1 and Procedure 2 presented in the U.S. Pharmacopoeia, despite containing only one stabilizer each—demonstrating that adding monothioglycerol, thiocyanate metal salt (preferably potassium salt) or dimethylthiourea, unlike prior art, can successfully reduce the amount of impurities formed from decomposition of donepezil in percutaneous absorption preparations.

Of the impurities of donepezil disclosed in the U.S. Pharmacopoeia, three can be identified using Procedure 1 and five can be identified with Procedure 2. Only one impurity, desbenzyl donepezil, is identified by both Procedure 1 and Procedure 2. The rest of the impurities identified by Procedures 1 and 2 do not overlap with each other. The acceptance criteria for controlling these impurities are set based on the toxicity of each impurity.

The inventors of the present invention found that employing only one of the two methods (Procedures 1 and 2) of donepezil impurity analysis cannot successfully test for all of the various impurities that are formed from decomposition of donepezil. Indeed, comparative example 16 met all of the acceptance criteria of Procedure 1 while exceeding the limit for an unidentified impurity with Procedure 2. Administering a donepezil formulation containing such an unidentified impurity may result in problems that arise from the potential toxicity of the unidentified impurity.

Therefore, the inventors of the present invention recognized the need for a stabilizer that can effectively reduce all of the impurities of donepezil tested for by both Procedure 1 and Procedure 2. The present inventors have found that adding monothioglycerol, thiocyanate metal salt (preferably potassium salt), or dimethylthiourea as a stabilizer, as in Examples 1 through 3, can successfully and effectively inhibit the formation of donepezil impurities covered by both Procedure 1 and Procedure 2.

The invention claimed is:

1. A percutaneous absorption preparation comprising a support layer, a drug-containing layer, and a release layer, wherein: the drug-containing layer comprises donepezil or a pharmaceutically acceptable salt thereof as an active ingredient, and a stabilizer selected from the group consisting of thiocyanate metal salt and dimethylthiourea, wherein a range of weight percentage of the stabilizer is from 0.0005% wt to 5% wt.

2. The percutaneous absorption preparation according to claim 1, wherein the donepezil is in a form of a free base.

3. The percutaneous absorption preparation according to claim 1, wherein the thiocyanate metal salt used as a stabilizer is potassium thiocyanate.

4. A method of preparing the percutaneous absorption preparation comprising donepezil according to claim 1, wherein the method comprises the steps of: i) dissolving donepezil, or a pharmaceutically acceptable salt thereof, and a stabilizer in an organic solvent, said stabilizer being thiocyanate metal salt or dimethylthiourea, wherein a range of weight percentage of the stabilizer is from 0.0005% wt to 5% wt; ii) applying the solution obtained in step i) onto a release layer and drying to form a drug-containing layer; and iii) laminating the drug-containing layer obtained in step ii) with a support layer.

5. The method of claim 4, wherein the organic solvent is selected from the group consisting of ethyl acetate, toluene, hexane, 2-propanol, methanol, ethanol, methylene chloride, and tetrahydrofuran.

* * * * *